United States Patent [19]

Wirtzfeld et al.

[11] 4,202,339
[45] May 13, 1980

[54] CARDIAC PACEMAKER

[75] Inventors: Alexander Wirtzfeld, No. 26b, Haupstrasse, 8191 Thanning; Thomas Bock, Munich, both of Fed. Rep. of Germany

[73] Assignee: Alexander Wirtzfeld, Thanning, Fed. Rep. of Germany

[21] Appl. No.: 970,894

[22] Filed: Dec. 19, 1978

[51] Int. Cl.$^2$ .............................................. A61N 1/36
[52] U.S. Cl. ............................... 128/419 PG; 128/634
[58] Field of Search ...... 128/142 R, 419 PG, 633 PS, 128/634, 653, 664, 665

[56] References Cited

U.S. PATENT DOCUMENTS

| | | | |
|---|---|---|---|
| 3,478,746 | 11/1969 | Greatbatch | 128/419 PG |
| 3,593,718 | 7/1971 | Krasner et al. | 128/419 PG |
| 3,734,091 | 5/1973 | Taplin | 128/142 |
| 3,814,081 | 6/1974 | Mori | 128/634 |
| 3,847,483 | 11/1974 | Shaw et al. | 128/634 |
| 4,009,721 | 3/1977 | Alcidi | 128/419 PG |

FOREIGN PATENT DOCUMENTS 2609365  9/1977  Fed. Rep. of Germany .... 128/419 PG

*Primary Examiner*—William E. Kamm
*Attorney, Agent, or Firm*—John C. Smith, Jr.

[57] ABSTRACT

A cardiac pacemaker includes means for conforming the stimulation frequency to the bodily stressing conditions of the wearer of the pacemaker in using a blood parameter as measuring value for the influencing of the frequency of stimulation. A measuring probe is implanted in the heart of the wearer of the pacemaker for measuring the oxygen saturation of the blood. The measuring value thereby resulting serves as measuring parameter for the influencing of the frequency of stimulation.

9 Claims, 7 Drawing Figures

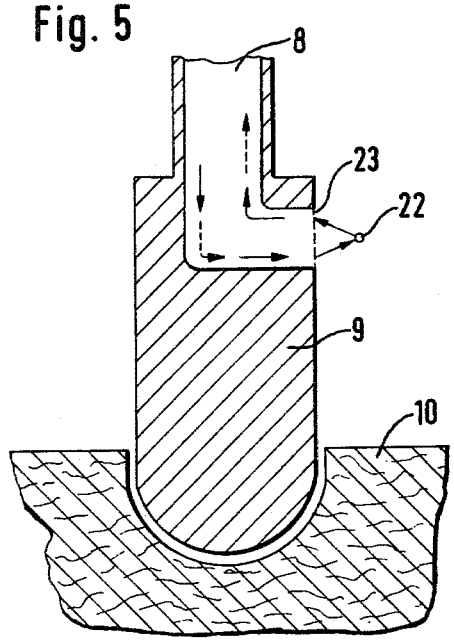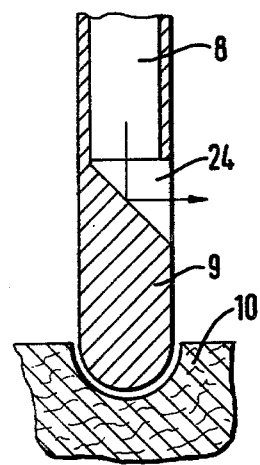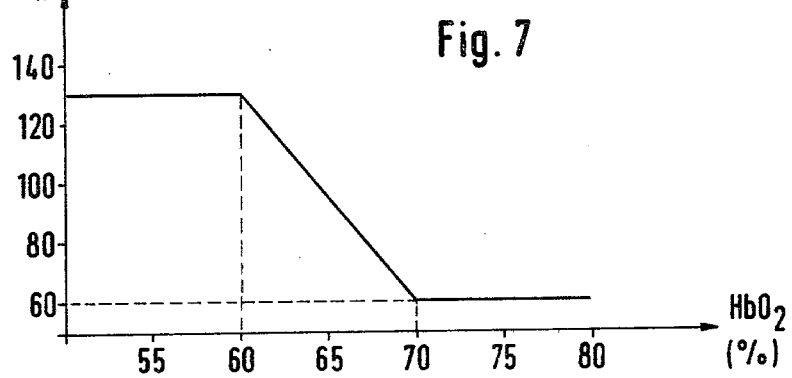

CARDIAC PACEMAKER

THE PRIOR ART

U.S. Pat. No. 4,009,721 and German Auslegungsschrift No. 2,215,984 have been cited by the Examiner in the course of the examination procedure of the corresponding German patent application Ser. No. 27 17 659.6.

BACKGROUND OF THE INVENTION

This invention relates to a cardiac pacemaker including means for controlling the stimulation frequency conformed to the bodily stressing conditions of the wearer of the pacemaker. The electro-stimulation of the heart today is that therapy of selection of a number of bradycardic disturbances of the cardiac rhythm, which can hardly or at least not on the long run be influenced by medicamentous treatment and the prognosis of which were very serious prior to the employment of pacemakers. The primary goal of pacemaker employment initially was to prevent the cardiac standstill (asystole) which caused loss of conciousness occurring in attacks, often with the consequences of a stroke or even with a fatal end. This goal has today broadly been achieved, and the pacemaker method is practiced with great success for patients having such syndromes, everywhere.

A second indication for the cardiac pacemaker therapy to an increasing degree is the bradycardiac insufficiency, i.e. the development of heart weakness by virtue of an insufficient frequency regulation. For while the sound heart by increasing the heart frequency is able to increase its performance according to the bodily requirements, heart-sick patients with bradycardic heart rhythm disturbances in many instances are not able to do so any more. The form of cardiac pacemaker stimulation performed up to now also brings about no decisive improvement in this aspect, since the frequency of stimulation (generally 70/min) is fixed and is not variable.

Therefore, there has been no lack of attempts to control the pacemaker stimulation frequency via physiological parameters such as the frequency of breathing or the pH of the venous blood, with the aim of increasing the frequency of stimulation with a corresponding alteration of these parameters. These systems give rise to a number of new problems, however:

The implantation of a pacemaker controlled by the frequency of breathing requires a thoracotomy for implanting a pressure sensor into the pleural cavity, which is an unequally more serious operation as compared with the usual operation method of transvenous electrode displacement.

For the pH controlled pacemaker, the problem of a reliable pH measurement over extended periods of time has not been completely solved up to now. Additionally, the pH cannot be considered to be an optimum parameter for controlling the frequency of the cardiac pacemaker, since this parameter is not only dependent on the heart time volume, but also on other parameters such as breathing, the buffer capacity of blood, the kidney function and the application of certain medicines.

SUMMARY OF THE INVENTION

In order to avoid these deficiencies it is the object of the present invention to provide a cardiac pacemaker including means for conforming the stimulation frequency to the bodily stressing conditions of the wearer of the pacemaker in using a blood parameter as measuring value for the influencing of the frequency of stimulation, said cardiac pacemaker comprising a measuring probe being implanted in the heart of the wearer of the pacemaker for measuring the oxygen saturation of the blood, the measuring value thereby resulting serving as measuring parameter for the influencing of the frequency of stimulation.

The proposed cardiac pacemaker uses the measurement of the blood oxygen saturation (abbrevations: $HbO_2$ for blood the hemoglobin of which is oxygen saturated, Hb for blood the hemoglobin of which is not oxygen saturated) for controlling the frequency of the pacemaker. The determination of the oxygen saturation by percent of the venous blood is a method practiced since long ago for calculating the heart time volume, i.e. the blood volume conveyed per minute by the heart pump. An insufficient conveying performance of the heart always via the mechanism of an increased oxygen exhaustion in the body periphery results in an oxygen undersaturation of the central venous blood, and therefore according to the invention this parameter is used as control parameter. The in vivo determination of the blood oxygen saturation via light conductor probes per se is known. Devices operating on this principle have been in use since about two years in cardiological guarded stations or in cardiac catheter laboratories.

BRIEF DESCRIPTION OF THE DRAWINGS

An embodiment of the invention will now be described by way of example and with reference to the accompanying drawings, in which:

FIG. 5 is an enlarged illustration of a distal catheter end;

FIG. 6 is an illustration similar to FIG. 5 with a prism, and

FIG. 7 is an idealized control characteristic line of the pacemaker generator.

DESCRIPTION OF THE PREFERRED EMBODIMENT

Figure 1:
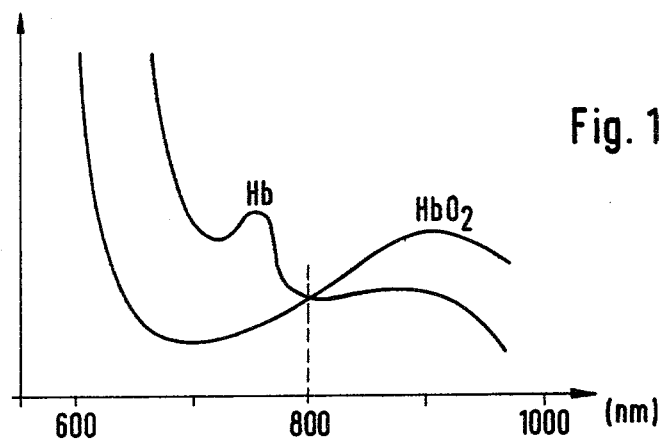
FIG. 1 is a diagram disclosing the dependency of the extinction coefficient on the wavelength of oxygen saturated and oxygen unsaturated hemoglobin.
Figure 2:
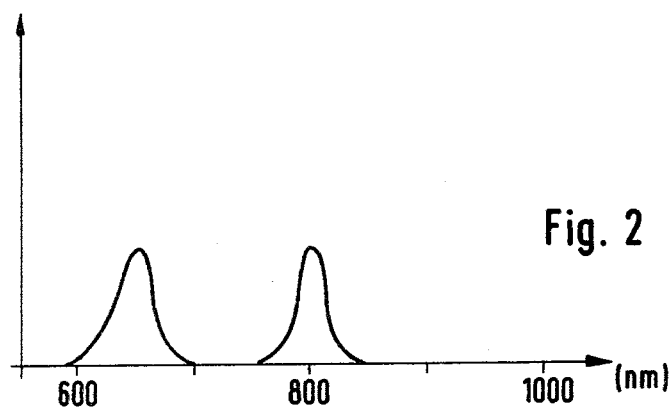
FIG. 2 are the emission spectra of the luminescence diodes.

The extinction (absorption and scattering) of light of the wavelength 660 nm for human blood is a function of the blood oxygen content thereof (FIG. 1). For eliminating interference effects (hematocrit, flow effects), next to the wavelength of 660 nm additionally a reference wavelength of 805 nm is used which are both generated by luminescence diodes. As FIG. 1 further illustrates, the reflexion of light of the wavelength 805 nm by flowing blood (statistical distribution of the blood corpuscles) is not dependent on the oxygen saturation thereof, in contradistinction to the wavelength 660 nm (intersection of Hb and $HbO_2$ curves at 805 nm). After evaluation of both reflexion intensities, as a result the $HbO_2$ saturation of the blood is obtained, with which the frequency of stimulation of the pacemaker is controlled after comparison with a reference value.

This in vivo oximetry method avoids practically any zeropoint drifting by virtue of the long-time constant light conductor catheters and luminescence diodes used and thus offers the condition required for the implantability of the pacemaker system controlled by blood oxygen saturation. For a detailed explanation of the circuitry function of the pacemaker, reference is had to FIGS. 3 and 4 which illustrate an embodiment by way of example. An oscillator 1 emits about one oscillation per minute in the swung-in condition of the control circuit. From this signal, a monoflop 2 produces a square-wave pulse of a duration of 0.5 ... 1 ms. This is fed to the driver stage 3 of a luminescence diode 6 with a light wavelength of 660 nm directly, and in a delay member 4 (two monoflops in series, the first one causing the delay and the second regenerating the original pulse) it is delayed by the time $\tau$ and fed to the driver stage 5 of a luminescence diode 7 with a light wavelength of 805 nm. The light flashes generated in these diodes pass on, time-shifted by $\tau$ relative to one another, along a common fiber light conductor 8 which is placed transvenously to the right-hand ventricle heart muscle 10. At the distal catheter end, there is an optical opening 23 from which the light pulses are emitted and are returned reflected by the blood flow 22 via the light conductor 8 to an optical receiver 11. The reflected signals arriving there consecutively are fed to two controlled switches 12 and 13 which are respectively opened by the direct signal and by the signal delayed by $\tau$ from the monoflop 2 for the duration of the pulse. Ordered in this way, the reflexion signals pass to sample and hold circuits 14 and 15, in order to be passed on from there as denominator and numerator for a quotient formation to the inputs of a divison circuit 16. The result formed in this division circuit is the actual value of the blood oxygen saturation. In a functional block 18, a comparison of this actual value with the desired value supplied by a reference voltage generator 17 is performed. A resulting control deviation is used for influencing the frequency of a pacemaker oscillator 19 and at the same time serves to correlate the frequency of the blood oxygen saturation measurements to physiological conditions by also influencing the frequency of the oscillator 1 within predetermined limits. This intends to obtain a quicker controlling of desired value deviations of the blood oxygen saturation. The oscillations from the pacemaker oscillator 19 are now processed by the monoflop 20 into stimulation pulses and pass to a stimulation electrode 9 surrounding the fiber light conductor 8.

Figure 3:
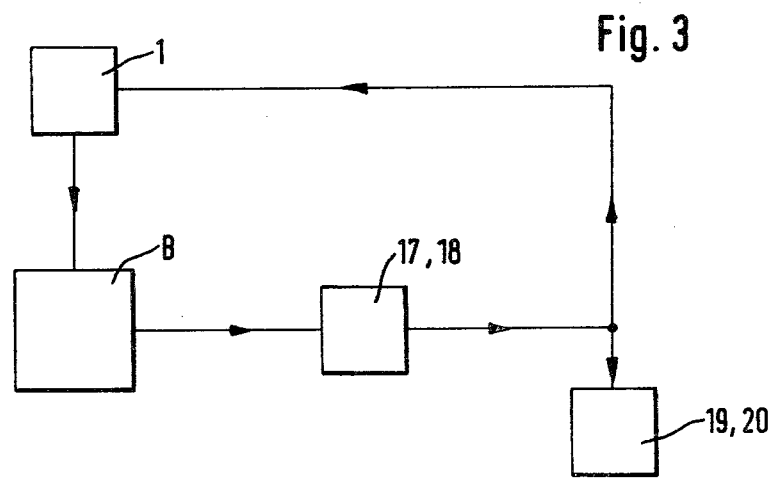
FIG. 3 is a block diagram of a pacemaker.
Figure 4:
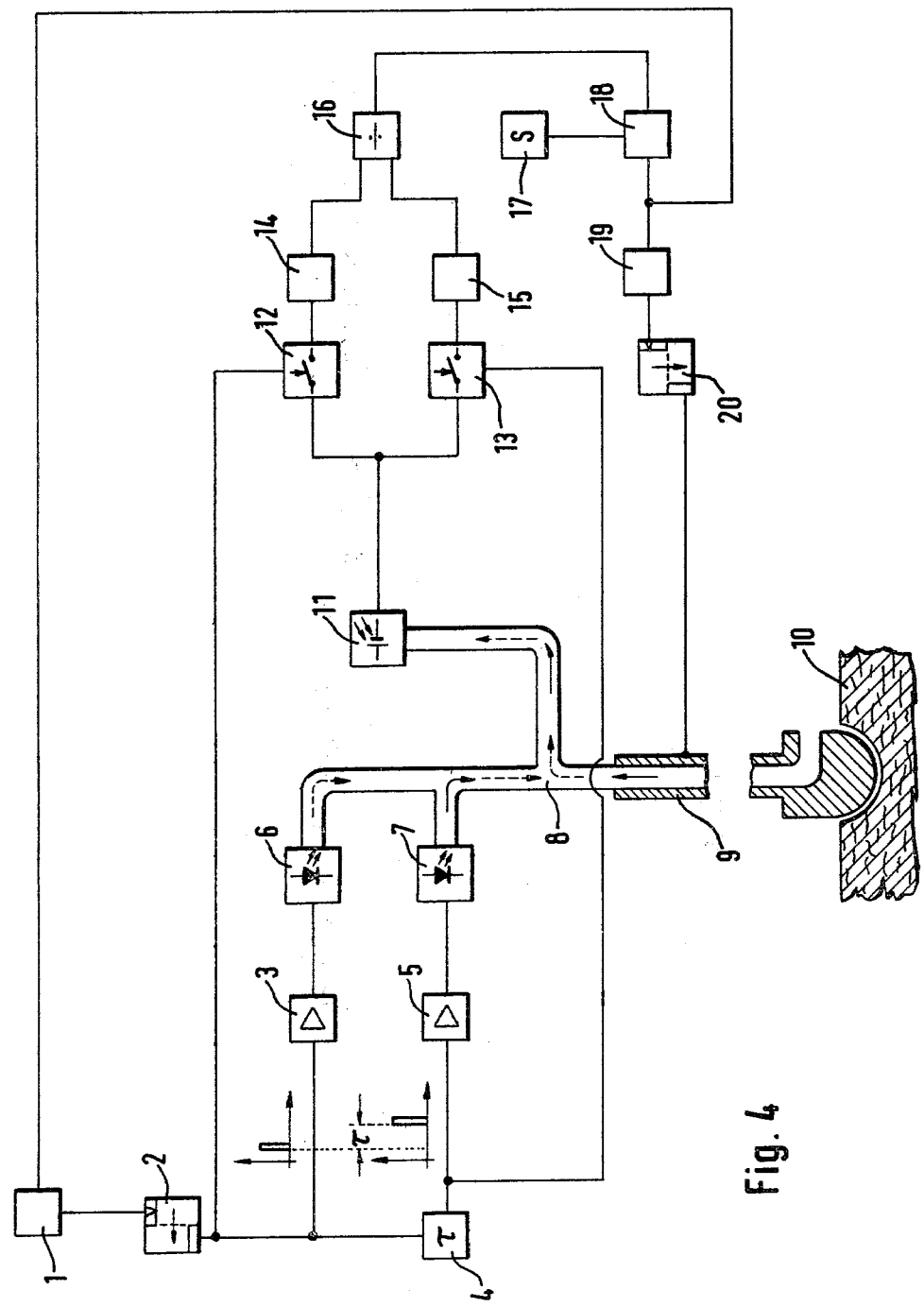
FIG. 4 is a circuit diagram of a pacemaker according to FIG. 3.

FIG. 3 is a simplified block circuit diagram of FIG. 4. In it, B indicates the circuit for the oxygen saturation measurement. FIG. 5 is a distal catheter end of the circuit according to FIG. 4.

The distal catheter end according to FIG. 6 possesses a prism 24 which serves the purpose of coupling in or out the radiation conducted in the light conductor. This is necessary for small catheter diameters (about 2 mm). Thereby, a smoother catheter surface may be obtained.

In FIG. 7, an example for an (idealized) control characteristic line of the pacemaker generator 19 influenced by the control deviation has been illustrated. The oxygen saturation of the blood is returned for the deviations occurring in practice of about −10% from the reference (desired) value (70%) by the alteration of the heart frequency $f_H$ and thus of the heart minute volume to this normal value. The adjustment parameter $f_H$ is proportional in the range of 60 ... 125 (1/min) to the blood oxygen saturation for a negative control deviation between 0 ... 10% from the desired value 70% (blood oxygen saturation).

The invention may be embodied in other specific forms without departing from the spirit or the essential characteristics thereof. The embodiment is therefore to be considered in all respects as illustrative and not restrictive.

What is claimed is:

1. A cardiac pacemaker including means for conforming the stimulation frequency to the bodily stressing conditions of the wearer of the pacemaker in using a blood parameter as measuring value for the influencing of the frequency of stimulation, said cardiac pacemaker comprising a measuring pole implanted in the heart of the wearer of the pacemaker for measuring the oxygen saturation of the blood, the measuring value thereby resulting serving as measuring parameter for the influencing of the frequency of stimulation.

2. A cardiac pacemaker according to claim 1, wherein the means for conforming the stimulation frequency to the bodily stressing conditions is a control circuit with a desired-actual value comparison.

3. A cardiac pacemaker according to claim 1, wherein the measuring probe operates on the principle of in vivo reflexion oximetry known per se and light sources having a measuring wavelength of about 660 nm and an additional reference wavelength of about 805 nm are provided.

4. A cardiac pacemaker according to claim 1, wherein means are provided which permit the oxygen saturation measurement only for a short period of time and in predetermined measuring intervals.

5. A cardiac pacemaker according to claim 4, wherein means are provided which vary the measuring intervals automatically dependent on the gradient of the blood oxygen saturation.

6. A cardiac pacemaker according to claim 1, wherein means are provided which permit a correlation of the desired value of oxygen saturation as well as the control characteristic of the control for the frequency of stimulation to the individual requirements of the wearer of the pacemaker.

7. A cardiac pacemaker according to claim 1, wherein the measuring probe and the stimulation electrode are defined by discrete catheters and are implantable separate from one another.

8. A cardiac pacemaker according to claim 1, wherein the measuring probe and the stimulation electrode are integrated in a single catheter.

9. A cardiac pacemaker according to claim 8, wherein the radiation conducted in the light conductor is capable of being coupled in and out via a prism.

* * * * *